United States Patent [19]

Dannels et al.

[11] Patent Number: 4,849,556
[45] Date of Patent: Jul. 18, 1989

[54] PROCESS FOR PREPARING TELOMERS FROM CHLOROTRIFLUOROETHYLENE AND TRIFLUOROTRICHLOROETHANE

[75] Inventors: Bobby F. Dannels; Deborah J. Olsen, both of Grand Island, N.Y.

[73] Assignee: Occidental Chemical Corporation, Niagara Falls, N.Y.

[21] Appl. No.: 116,843

[22] Filed: Nov. 5, 1987

[51] Int. Cl.$^4$ .................. C07C 17/26; C07C 19/08
[52] U.S. Cl. ................................ 570/172; 570/139
[58] Field of Search ..................... 570/172, 139

[56] References Cited

U.S. PATENT DOCUMENTS

| 2,462,402 | 2/1949 | Joyce | 570/172 |
| 2,700,661 | 1/1955 | Miller | 570/139 |
| 2,875,253 | 2/1959 | Barnhart | 570/139 |
| 3,843,734 | 10/1974 | Trebillon | 570/139 |
| 4,533,762 | 8/1985 | Campbell et al. | 570/139 |
| 4,577,044 | 3/1986 | Campbell et al. | 570/139 |

FOREIGN PATENT DOCUMENTS

| 576707 | 5/1959 | Canada | 570/139 |
| 93580 | 11/1983 | European Pat. Off. | 570/172 |
| 140385 | 5/1985 | European Pat. Off. | 570/139 |

Primary Examiner—J. E. Evans
Attorney, Agent, or Firm—James F. Tao; Richard D. Fuerle

[57] ABSTRACT

Telomers are prepared by reacting chlorotrifluoroethylene with 1,1,2-trichlorotrifluoroethane ($CCl_2FCF_2Cl$) in the presence of metallic iron or stainless steel, and optionally, a halide-containing compound selected from the group consisting of tetrabutyl ammonium bromide, tetramethyl ammonium chloride, n-chlorosuccinimide, triethylamine hydrochloride, LiCl, $MoCl_5$ and $FeCl_3$. The reaction is conducted at a temperature of from about 150° C. to about 200° C. in a nitrile group-containing solvent selected from the group consisting of acetonitrile, propionitrile and ethyl cyanoacetate. Preferably, the $CCl_2FCF_2Cl$ and chlorotrifluoroethylene are present in a mole ratio of from about 1:1 to about 3:1 respectively, to minimize the amount of high molecular weight species formed during the reaction. The telomers of this invention are useful for preparing non-flammable hydraulic fluids.

7 Claims, No Drawings

PROCESS FOR PREPARING TELOMERS FROM CHLOROTRIFLUOROETHYLENE AND TRIFLUOROTRICHLOROETHANE

BACKGROUND OF THE INVENTION

The present invention relates to a process for preparing telomers of the formula $CF_2ClCFCl(CF_2CFCl)_nCl$, where n is in the range of 1 to 10. The telomers of this invention are saturated, low molecular weight polymers which are useful for preparing non-flammable hydraulic fluids.

Various methods of preparing chlorotrifluoroethylene ("CTFE") telomers are known in the prior art and have been practiced commercially for many years. An article by William T. Miller, Jr. et al. in *Industrial and Engineering Chemistry*, pages 333–337 (1947), entitled "Low Polymers of Chlorotrifluoroethylene", describes a process for producing low molecular weight polymers of CTFE by polymerization in a solution of chloroform using benzoyl peroxide as a polymerization promoter. Other solvents disclosed in the reference as being useful for this purpose include carbon tetrachloride and tetrachloroethylene. The solution is heated in a pressure vessel for 1¾ hours at 100° C., and the unreacted CTFE monomer and chloroform are removed by distillation, leaving a crude telomer of general formula $CHCl_2(CF_2CClF)_nCl$, which can be further heated and distilled to yield products ranging from a light oil to a semi-solid wax or grease.

Another process for preparing low molecular weight CTFE polymers is described in U.S. Pat. No. 2,788,375, issued Apr. 9, 1957. This process comprises reacting CTFE with a saturated brominated compound in the presence of a source of radiation. Suitable brominated compounds include 1,2-dibromo-2-chlorotrifluoroethane ($CF_2BrCClFBr$). The saturated bromopolychlorofluoro compounds obtained by this process can then be distilled, and the isolated fractions reacted with chlorine to prepare polychlorofluoro compounds. The compounds are predominantly higher molecular weight telomers, i.e. n is greater than 4.

A more recent development in this field is described in a series of articles by Y. Pietrasanta et al. entitled "Telomerization by Redox Catalysis" appearing in the *European Polymer Journal*, Vol. 12 (1976). This technology involves the reaction of single carbon halogenated telogens, such as $CCl_4$ and $CCl_3Br$, with CTFE in the presence of benzoin and a suitable redox catalyst, such as ferric chloride. The telomerization reaction is suitably carried out in acetonitrile which is a common solvent for the reactants and catalysts. The telomerization reaction can be illustrated as follows:

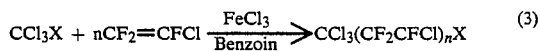

$$CCl_3X + nCF_2=CFCl \xrightarrow[\text{Benzoin}]{FeCl_3} CCl_3(CF_2CFCl)_nX \quad (3)$$

where X is chlorine or bromine. The reference further discloses that the use of $CCl_3Br$ as a telogen results in a lower degree of telomerization and a higher proportion of monoaddition product than would occur with the use of $CCl_4$.

The redox process has the advantage of directly preparing low molecular weight products without the necessity of cracking or fractionating a higher molecular weight polymer.

A modification of the redox process is disclosed in commonly assigned U.S. application Ser. No. 816,183, filed Jan. 6, 1986. In this modification, telomers of the formula $CF_2BrCFCl(CF_2CFCl)_nBr$, where n is in the range of 1 to 10, are prepared by reacting chlorotrifluoroethylene with 1,2-dibromo-2-chlorotrifluoroethane ($CBrClCF_2Br$) in the presence of a redox catalyst system. The redox catalyst system comprises a reducible metal halide selected from the group consisting of $FeCl_3$, $FeBr_3$, $CuBr_2$, $CuCl_2$, $TiCl_4$, $VCl_3$ and $NiCl_2$, and a reducing agent selected from the group consisting of Fe, Ni, Cu, Ti, V and benzoin, with the mole ratio of $CBrClCF_2Br$ to CTFE for this process typically being on the order of 1 to 3. This process has the advantage of being able to prepare CTFE telomers which can be readily separated into relatively pure, stable, low molecular weight isomers, which can be further chlorinated to prepare non-flammable hydraulic fluids.

Although telomers produced according to this latter process represent a significant advance over the prior art, there is still a need to increase the yield of the more desirable low molecular weight species. There is also a continuing need to develop less expensive telomerization processes by using of less costly reactants, and to eliminate cumbersome processing steps such as stabilization by post-chlorination or post-fluorination.

SUMMARY OF THE INVENTION

In accordance with the present invention, a distribution of telomers of the formula $CF_2ClCFCl(CF_2CFCl)_nCl$, where n is in the range of 1 to 10, are prepared by reacting chlorotrifluoroethylene with 1,1,2-trifluorotrichloroethane ($CF_2ClCCl_2F$) in the presence of a catalyst system comprising metallic iron or stainless steel type 410-L. The reaction mixture can optionally include a halide-containing compound, which functions as a chain-terminating agent, selected from the group consisting of LiCl, $FeCl_3$, $MoCl_5$, tetramethyl ammonium chloride, tetrabutyl ammonium bromide, triethylamine hydrochloride and n-chlorosuccinimide. The reaction is conducted in the presence of a nitrile group-containing solvent, and preferably acetonitrile, propionitrile or ethyl cyanoacetate.

The telomerization reaction of the present invention is conducted at a temperature of from about 150° C. to about 200° C., and a mole ratio of trifluorotrichloroethane to chlorotrifluoroethylene of from about 1 to 1 to about 3 to 1. This reaction produces a relatively high yield of low molecular weight species.

DESCRIPTION OF THE PREFERRED EMBODIMENTS

The telomerization process of the present invention involves the reaction of chlorotrifluoroethylene with 1,1,2-trifluorotrichloroethane ethane in a nitrile group-containing solvent, such as acetonitrile, propionitrile or ethyl cyanoacetate, in the presence of a catalytic amount of metallic iron or stainless steel type 410-L, which is an alloy of 87.5% iron and 12.5% chromium. Optionally, a halide-containing compound selected from the group consisting of LiCl, $FeCl_3$, $MoCl_5$, tetramethyl ammonium chloride, tetrabutyl ammonium bromide, triethylamine hydrochloride and n-chlorosuccinimide, can also be added to the reaction mixture. The halide-containing compound functions as a chain-terminating agent during the reaction to limit the formation of higher molecular weight species. This process can be illustrated as follows:

$$CF_2ClCCl_2F + nCF_2\!=\!CFCL \rightarrow CF_2ClCFCl(CF_2CFCl)_nCl, \quad (4)$$

where n is in the range of 1 to 10.

Reaction (4) results in the preparation of a mixture or distribution of individual telomer species having molecular weights corresponding to n values of from 1 to 10, rather than pure isomers having a discrete structure, i.e. a single n value. Separation of the individual telomer species from the mixture is accomplished by distillation using procedures well known to those skilled in this art.

Trifluorotrichloroethane, which is one of a number of Freon compounds, specifically Freon 113, is a readily available and comparatively inexpensive compound (Freon is a trademark of E. I. duPont DeNemours and Company). Although readily available, this compound has a low reactivity under telomerization reaction conditions such as those employed using $CCl_4$ or $CF_2BrCFClBr$ as telogens as discussed previously in connection with the preparation of telomers from these telogens. Under these reaction conditions, the conversion or yield of telomers using trifluorotrichloroethane as a telogen is only a few percent. Consequently, it is necessarily to modify these reaction conditions substantially in order to obtain a satisfactory yield of telomer product. This is accomplished by employing a halide-containing compound as indicated above, by increasing the reaction temperature to a range of from about 150° C. to 200° C., and by increasing the mole ratio of telogen to chlorotrifluoroethylene from a previously used 1 to 3 ratio to about 1 to 1 or 3 to 1. The altered mole ratio has the effect of limiting the formation of higher molecular weight telomer species which have little commercial value.

Following the process of the present invention, it has been found that a substantial proportion of lighter molecular weight telomer, i.e. in particular, the telomer species having an n value of 1, is produced in reaction (4). Although this telomer species has no known commercial value, it can be readily returned or recycled to the telomerization reaction, and thereby converted into useful telomer products of higher molecular weight, thus increasing the overall efficiency of the reaction.

It has been found that a relatively small amount of the high molecular weight products are formed in reaction (4), and that there is accordingly little waste of material. An additional advantage of this result is that processing of reactants and products is not complicated by the need to handle solid telomers or highly viscous materials. The desired telomer species, i.e. those having n values of 2 to 4, can thus be prepared in relatively high yield. These telomer species are of current interest as nonflammable hydraulic fluids.

In addition to the primary. and desired telomers produced in reaction (4), a minor amount of by-products, primarily unsaturated telomers, may also be produced in this reaction. These by-products can be eliminated by post-chlorination or fluorination.

The concentration of metallic iron or stainless steel 410-L in the reaction mixture typically is in the range of from about 0.1% to about 5% by weight of CTFE, and the concentration of halide-containing compound in the reaction mixture typically is in the range of from about 0.5% to about 10% by weight of CTFE.

The metallic iron or stainless steel 410-L used in the reaction is preferably in finely divided or powdered form. The powdered iron can be uniformly dispersed in the reaction vessel by means of mechanical agitation, such as in a stirred reactor.

Surprisingly, metals other than iron have been substituted for iron in reaction (4), but in all cases only a trace of the desired product was formed. This is illustrated in Examples 4-7 for nickel, cobalt, manganese and copper, respectively.

The following examples are intended to further illustrate the various embodiments and advantages of the present invention without limiting it thereby. These examples illustrate the preparation of CTFE telomers using various catalysts and solvents.

EXAMPLE 1

5 Grams of iron powder and 12 grams of lithium chloride were charged to a one-gallon glass-lined agitated kettle which was capable of withstanding internal pressures of up to 750 psi. The reactor contained a jacket through which oil was circulated to heat or cool it. After pressure-testing with nitrogen to 550 psi (this flushed most of the oxygen from the vessel), 1763 grams of Freon 113 (1,1,2-trichlorotrifluoroethane), 692 grams of acetonitrile and 565 grams of chlorotrifluoroethylene were added. The reactor was then heated to 180° C. This took 30 minutes and the pressure reached 450 psi. After reaching this temperature and pressure, an additional 5 grams of iron powder was added every 30 minutes. An additional 450 grams of chlorotrifluoroethylene was added in 3 portions whenever the pressure fell to about 410 psi. The reaction was continued for 5.5 hours.

After cooling, the volatile material was vented into a cold receiver and saved for recycle to the next run. The reaction mixture was discharged and then distilled. The lower boiling materials were separated at atmospheric pressure and included chlorotrifluoroethylene, acetonitrile, Freon 113, various by-products, and most of the four-carbon telogen product. This fraction was recycled to the next run.

The residual crude product was filtered while hot to remove the iron salts. The filter cake was washed with Freon 113 to recover adhered product. After stripping, the Freon 113 was used for the next run while the recovered product was combined with the filtrate. This was then distilled under reduced pressure to obtain a telomer fraction having from 6 to 18 carbon atoms.

The amount of telomers produced can be summarized as follows.

| | |
|---|---|
| 4 Carbon Telomer | 258 grams |
| 6-18 Carbon Telomer Fraction | 504 grams |
| >18 Carbon Telomer Fraction | 91 grams |

The 4-carbon telomer was purified by fractional distillation. Nuclear magnetic resonance (NMR) showed that this material was primarily 1,2,4,4-tetrachloro-1,1,2,3,3,4-hexafluorobutane. There was less than 1% of other isomers present.

Similarly, NMR analysis showed that the next two higher telomers were predominantly of the structure $Cl(CF_2CFCl)_nCl$.

EXAMPLE 2

12 Grams of lithium chloride was charged to the reactor of Example 1. After pressure-testing the reactor with nitrogen to 500 psi (this flushed most of the oxygen from the vessel), 1637 grams of the 4-carbon telomer prepared as in Example 1, 609 grams of acetonitrile and 340 grams of chlorotrifluoroethylene were added to the reactor. The reactor was then heated to 180° C. This took 30 minutes and the pressure reached 310 psi. After reaching this temperature and pressure, 5 grams of iron powder was added, and an additional 5 grams of iron powder was added every 30 minutes. An additional 500 grams of chlorotrifluoroethylene was added in 5 portions in order to maintain the pressure in the range of about 320 psi to 350 psi. The reaction was continued for 5 hours.

After cooling, the volatile material was vented into a cold receiver and saved for recycle to the next run. The reaction mixture was discharged and then distilled. The lower boiling materials were separated at atmospheric pressure and included chlorotrifluoroethylene, acetonitrile, Freon, various by-products, and some of the 4-carbon telogen. This fraction was recycled to the next run.

The residual crude product was filtered while hot to remove the iron salts. The filter cake was washed with Freon 113 to recover adhered product. After stripping, the Freon 113 was used for the next run while the recovered product was combined with the filtrate. This was then distilled under reduced pressure to obtain a telomer fraction, having from 6 to 18 carbon atoms, which weighed 701 grams. The distillation residue amounted to 132 grams.

EXAMPLE 3

125 Grams of Freon 113, 75 grams of acetonitrile, 0.6 grams of tetrabutyl ammonium bromide, and 3.5 grams of iron powder were charged with stirring into a 600 ml glass lined autoclave. After pressurechecking and flushing with $N_2$, 117 grams of chlorotrifluoroethylene was added. The autoclave was closed and slowly heated to 180° C. The reaction was maintained at this temperature for 4 hours. The maximum pressure reached was 505 psig, and the pressure fell to 350 psig at the end of the reaction. The reactor was then cooled to room temperature, and unreacted chlorotrifluoroethylene was vented off.

Upon opening the autoclave, 252 grams of reaction mixture was obtained which consisted of two liquid phases. This product was washed with dilute HCl and then with water. Gas chromotograph (GC) analysis of the washed product indicated that approximately 30% of the Freon 113 had reacted to form telomers that ranged in molecular weight from 4-carbon to 20-carbon species. The relative amount of each telomer decreased as the molecular weight increased.

EXAMPLE 4

100 Grams of Freon 113, 75 grams of acetonitrile, 0.6 grams of tetrabutyl ammonium bromide, and 3.3 grams of nickel powder were charged with stirring into a 600 ml glass lined autoclave. After pressure-checking and flushing with nitrogen, 120 grams of chlorotrifluoroethylene was added. The autoclave was closed and slowly heated to 200° C. The reaction was maintained at this temperature for 4 hours, and the maximum pressure reached was 640 psig. The autoclave was then cooled to room temperature, and the unreacted chlorotrifluoroethylene vented off.

Upon opening the autoclave, 173 grams of reaction mixture was obtained. This product was washed with dilute HCl and then with water. GC analysis of the washed product indicated that less than 1% of the Freon 113 had reacted to form telomers.

EXAMPLE 5

Example 4 was repeated using cobalt in place of nickel. The crude product weighed 209 grams and consisted of solid suspended in liquid. GC analysis of the liquid showed that only a trace of the desired soluble telomers had been formed.

EXAMPLE 6

Example 4 was repeated using manganese in place of nickel. The crude product weighed 230 grams and consisted of 117 grams of solid suspended in a liquid. GC analysis of the liquid showed that only a trace of the desired soluble telomers had been formed.

EXAMPLE 7

Example 4 was repeated using copper in place of nickel. The crude product weighed 185 grams. GC analysis of the liquid showed that only a trace of the desired soluble telomers had been formed.

EXAMPLE 8

Example 3 was repeated by replacing the tetrabutyl ammonium bromide with the following halogen-containing compounds: tetramethyl ammonium chloride, n-chlorosuccinimide, triethylamine hydrochloride, lithium chloride, molybdenum pentachloride, and ferric trichloride. In all cases, the results were similar. It has been observed that if these components are omitted from the reaction mixture, the telomer distribution is shifted toward the generation of higher molecular weight telomer products.

EXAMPLE 9

Example 3 was repeated by replacing acetonitrile with one of the following: propionitrile, ethyl cyanoacetate, DMF, THF, ethyl acetate, and ethyl acetonitrile. In the case of propionitrile and ethyl cyanoacetate, the product was similar to that obtained in Example 3. In all other cases, little or none of the desired telomers were formed.

While various embodiments and exemplifications of this invention have been shown and described in the specification, modifications and variations thereof will be readily appreciated by one skilled in the art. It is to be understood, therefore, that the appended claims are intended to cover all such modifications and variations which are considered to be within the scope and spirit of the present invention.

What is claimed is:

1. A process for preparing a distribution of telomers of formula $CF_2ClCFCl(CF_2CFCl)_nCl$, where n is in the range of 1 to 10, comprising reacting chlorotrifluoroethylene with $CF_2ClCFCl_2$ in the presence of metallic iron, said reaction being conducted at a temperature of from about 150° C. to 200° C. in a nitrile group-containing solvent selected from the group consisting of acetonitrile, nitrile and ethyl cyanoacetate, and a halide-containing compound selected from the group consisting of tetrabutyl ammonium bromide, tetramethyl ammonium chloride, n-chlorosuccinimide, triethylamine hydrochloride, LiCl, and $MoCl_5$.

2. The process of claim 1 wherein the halide-containing compound is LiCl.

3. The process of claim 1 wherein the $CF_2ClCFCl_2$ and chlorotrifluoroethylene are present in mole ratios of from about 1 to 1 to about 3 to 1, respectively.

4. The process of claim 1 wherein the solvent is acetonitrile.

5. The process of claim 1 wherein the telomer having an n value of 1 is recovered and recycled to the reaction mixture.

6. The process of claim 1 wherein the metallic iron is present in the reaction mixture in an amount of from about 0.1% to about 5% by weight of chlorotrifluoroethylene.

7. A process for preparing a distribution of telomers of formula $CF_2ClCFCl(CF_2CFCl)_nCl$, where n is in the range of 1 to 10, comprising reacting chlorotrifluoroethylene with $CF_2ClCFCl_2$ in the presence of stainless steel type 410-L, said reaction being conducted at a temperature of from about 1500° C. to about 200°C. in a nitrile group-containing solvent selected from the group consisting of acetonitrile, propionitrile and ethyl cyanoacetate, and a halidecontaining containing compound selected from the group consisting of tetrabutyl ammonium bromide, tetramethyl ammonium chloride, n-chlorosuccinimide, triethylamine hydrochloride, LiCl, and $MoCl_5$.

* * * * *